United States Patent [19]

Thame

[11] Patent Number: 4,952,392
[45] Date of Patent: * Aug. 28, 1990

[54] USE OF PERIWINKLE IN ORAL HYGIENE

[75] Inventor: Neville Thame, Montclair, N.J.

[73] Assignee: Peri-Oral Dental Products, Inc., Taos, N. Mex.

[*] Notice: The portion of the term of this patent subsequent to Aug. 1, 2006 has been disclaimed.

[21] Appl. No.: 387,083

[22] Filed: Jul. 27, 1989

Related U.S. Application Data

[63] Continuation-in-part of Ser. No. 168,989, Mar. 16, 1988, Pat. No. 4,853,213, which is a continuation of Ser. No. 840,019, Mar. 17, 1986, abandoned.

[51] Int. Cl.$^5$ .......................... A61K 7/26; A61K 7/16; A61K 7/18
[52] U.S. Cl. ......................................... 424/58; 424/49; 424/52; 424/55; 424/56; 424/57; 514/900; 514/901; 514/902
[58] Field of Search ...................... 424/49, 58, 55–57; 514/900–902

[56] References Cited

U.S. PATENT DOCUMENTS

| | | | |
|---|---|---|---|
| 3,119,743 | 1/1964 | Ericsson | 424/52 |
| 3,888,976 | 6/1975 | Mikvy | 424/44 |
| 4,853,213 | 8/1989 | Thame | 424/58 |

OTHER PUBLICATIONS

Derwent Abst., C85-107166 of J6 0163.810-A, Aug. 1985.
Derwent Abst., C84-025172 of J5 9016.814-A, Jan. 1984.
Chem. Abst., 104, 304 (1986), Abst. No. 10428a.
Chem. Abst., 103, 301 (1985), Abst. No. 11246f.
Chem. Abst., 99, 327 (1983), Abst. No. 200365d.
Chem. Abst., 84, 350 (1976), Abst. No. 140622p.
Grieve, A Modern Herbal, vol. II, Dover Publication, 1982, pp. 629–631.
John Lust, The Herb Book, Bantam Books, p. 333.
Robertson, Diane; Jamacian Herbs, 1982, 1 page.
Eli Lilly Co.; "VELBAN" fact sheet; (2 pages).
Eli Lilly Co.,; "ONCOVIN" fact sheet; (2 pages).
Tokumaru and Avitabile, "Suppression of Herpes Simplex Virus Infection by Antimitotic Substances in the Rabbit Cornea"; Proc. Soc. Exp. Biol. Med.; 1971; pp. 29–34.
Boulware, R. T. and Southard, G. L., "Sanguinarine in the Control of Volatile Sulfur Compounds in the Mouth: A Comparative Study"; Compendium of Continuing Education in Dentistry; 1984; Supplement No. 5; S61–A64.
Yankell, S. L.; "Saliva Glycolysis and Plaque", Compendium of Continuing Education in Dentistry; 1984; Supplement No. 5; pp. S57–S60.
Hutchinson, J.; The Families of Flowering Plants; 1959; vol. I, 2nd Ed.; pp. 75–83, 96–99, 178–179, 380–381.
Jaques, H. E.; Plant Families How to Know Them; 1949; 2nd Ed.; pp. 138–139, 144–145, 154–163.
Gleason, Henry A., Ph.D. and Cronquist, Arthur, Ph.D.; Manual of Vascular Plants of Northeastern United States and Adjacent Canada; 1963; pp. 554–555, 654–657.
G. Garnier et al.: "Ressources Medicinales de la Flore Francaise", Tome II, 1961, Vigot Freres Editeurs (Paris, FR), pp. 1007–1011.

Primary Examiner—F. T. Moezie
Attorney, Agent, or Firm—Samuelson & Jacob

[57] ABSTRACT

Oral hygiene methods and compositions for reducing plaque and for the prevention and treatment of periodontal diseases of bacterial etiology by significantly reducing bacterial activity in the oral cavity through the inclusion of at least about 0.03% by weight of an extract of the perennial herb periwinkle in the compositions and applying the compositions to the oral cavity.

8 Claims, No Drawings

USE OF PERIWINKLE IN ORAL HYGIENE

This application is a continuation-in-part of application Ser. No. 168,989, filed Mar. 16, 1988, now U.S. Pat. No. 4,853,213 which is a continuation of application Ser. No. 840,019, filed Mar. 17, 1986, now abandoned.

FIELD OF THE INVENTION

The invention relates to oral hygiene compositions and their use for reducing dental plaque and for the treatment of periodontal diseases of bacterial etiology.

BACKGROUND OF THE INVENTION

Periodontal disease is a plaque-generated condition involving attack on the gum structure around the tooth and the bone which supports that tooth. The disease is very prevalent. In general, it has been observed that in the normal, nondiseased human mouth the gums have a light-pink, healthy, noninflamed complexion. If not kept relatively free of dental plaque, however, the gums become red and puffy, and bleed readily when the teeth are brushed. This is the first indication of gingival disease, and the condition is classified as gingivitis. Gingivitis may or may not lead to more advanced periodontal disease states. However, it has been observed that the sites of more advanced periodontal disease, for example deep periodontal pockets, usually develop only in those areas where gingivitis has occurred. The average person is not able to recognize the symptoms of gingival disease as a potential precursor of serious dental problems. It thus is necessary to provide means to enhance gingival integrity on a continuing basis.

Dental plaque is recognized as the cause of gingival disease and dental caries. Plaque may be classified as supragingival plaque or subgingival plaque, i.e. above and below the gingival margin, respectively. The plaque consists of massed bacteria. It is observable as a gelatinous deposit on the teeth, characterized by being soft, sticky, insoluble in water, and adherent. Toxins including acids, generated by the microbial residents of the plaque, are responsible for the deleterious effects of the plaque.

The bacterial flora of the plaque is variable. Supra- and subgingival plaque harbor different bacterial flora. Both gram-positive and gram-negative organisms occur. The complexity of the bacterial flora makes attack on the total plaque by agents directed at specific microorganisms relatively fruitless as a means of plaque control for the average individual. Total nonspecific plaque removal or inhibition has thus been accepted as the practical approach to dental plaque control. This approach includes toothbrushing and the regular application of broad spectrum antimicrobial agents.

Chemicals extracted from the periwinkle plant (*Vinca major, Vinca minor* and *Vinca rosea*) have found extensive use in the treatment of many ailments. It ha been shown that two of the active compounds in this plant are dimeric alkaloids known as vincristine and vinblastine, sold under the names of "ONCOVIN ®" and "VELBAN ®", respectively. Numerous studies have demonstrated the use of these two extracts in the treatment of various form of cancer. For example, vincristine has been used in the treatment of acute leukemia and may be used in combination with other oncolytic agents for the treatment of Hodgkin's disease, lymphosarcoma, reticulum-cell sarcoma, rhabdomyosa coma, neuroblastoma and Wilm's tumor. Vinblastine is indicated in the treatment of Hodgkin's disease, Kaposi's sarcoma, mycosis fungoides, various types of lymphomas, and other carcinomas.

Vincristine and vinblastine have been shown to be capable of suppressing herpes simplex virus infections. (Tokumaru and Avitabile, *Proc. Soc. Exp. Biol. Med.,* 1971). U.S. Pat. No. 4,328,231 discloses a class of compounds, at least some of which can be isolated from *Vinca minor*, useful in treating skin diseases such as psoriasis.

Folklore has attributed curative properties to the periwinkle plant. It has been recommended as a remedy for diarrhea and hemorrhages. A tea made from the plant can be used for nervous conditions. It was thought to be a cure for diabetes. Chewing the herb has been recommended to stop toothache or to stop bleeding in the mouth and nose. Another source also reports its use as a laxative, for cramps, and for skin inflammation, and suggests the use of Vinca major as a gargle in cases of scurvy, sore throat and inflamed tonsils.

Co-pending application Ser. No. 168,989 now U.S. Pat. No. 4,853,213, issued Aug. 1, 1989 relates to the use of a methanol extract of periwinkle as an antibacterial agent effective against microorganisms associated with plaque-caused oral disease and malodor.

The present invention is directed to the use of an ethanol extract of periwinkle for several oral hygiene purposes. These include plaque reduction, control of volatile sulfur compounds (which is related to breath freshening), cleaning of the teeth and conditioning of gum tissue, and relieving the symptoms of gingivitis. The ethanol extract appears to possess antimicrobial properties, especially when used in combination with an anionic surfactant such as sodium lauryl sulfate.

SUMMARY OF THE INVENTION

The present invention relates to compositions which are useful and convenient for improving various aspects of oral hygiene. These compositions, which may be used in tooth cleansing and mouthwash formulations, comprise an extract from the perennial herb periwinkle (*Vinca major, Vinca minor* or *Vinca rosea*), also known as myrtle and ramgoat roses.

The tooth cleansing composition may be in the form of toothpaste, tooth powder or mouthwash, or any form suitable for use in the oral cavity, including a salve, breath spray or chewing gum, but for ease of application, the toothpaste and mouthwash are preferred. The compounds of the invention may also be coated on oral hygiene accessories, such as dental floss.

The extract of periwinkle is compatible with other agents commonly found in toothpaste, and then formulated with them, it does not possess the bitter sharp and burning taste of the plant.

In order to obtain the beneficial effects of the periwinkle extract, its concentration may vary preferably from about 0.03% to about 50% by weight, but more preferably from about 0.03% to about 10%, in the toothpaste and mouthwash formulations.

DETAILED DESCRIPTION OF THE INVENTION

The periwinkle extract useful in this invention is obtained from the periwinkle plant. One method of preparation comprises harvesting and drying the plant grinding the dried plant, and extracting the ground material with an alcohol such as ethanol or methanol. The alcohol extract is separated and carefully evaporated. The residue is then taken up in a suitable solvent, such as a mixture of water, alcohol and glycerin. Other methods and materials for preparation of the extract can be employed, observing the conventional precautions for the preparation of biological extracts. For instance, the extract of per winkle is preferably produced by slurrying the finely divided dried plant and extracting it with methanol or ethanol at elevated temperatures. For example, the finely divided dried plant is mixed with the alcohol and stirred at 60° C. for approximately 3 hours. The alcohol is separated through filtration and then evaporated to dryness. The residue is dissolved in chloroform and made acidic by the addition of concentrated hydrochloric acid. In some instances it s preferable to use the periwinkle extract without acidification; such as in the case when it is formulated with sodium bicarbonate. The mixture is filtered and subsequently the filtrate is evaporated to dryness. The periwinkle extract is preferably light in color, and usually is light amber to amber in color. The depth of color is determined in part by the extraction procedure and subsequent processing procedures. Observance of precautions used to prepare biological concentrates in general will provide a periwinkle extract suitable for formulation into oral care products.

The flavor of the periwinkle extract usually is not unpleasant. It lacks the characteristic bitterness associated with cationic antimicrobials. It may have a slight taste of burnt sugar, probably due to some caramelization during processing. This taste is not associated wi h efficacy, and, if present, is readily hidden by appropriate flavoring agents.

After the evaporation to dryness, the solid extract may be combined with solvent materials such as ethanol or glycerin. Convenient preparations are primarily aqueous, containing small amounts of carriers such as ethanol and glycerin, as described in the formulas for Additives A and B, below.

Additives are made by combining the periwinkle extract with other ingredients such as ethanol, glycerin and water. Examples of these Additives are as follows:

| Component | % by Wt. |
|---|---|
| Additive A | |
| Glycerin | 87.8 |
| Water (distilled) | 11.0 |
| Sodium Bicarbonate | 0.65 |
| Alcohol Extract of Periwinkle | 0.55 |
| Additive B | |
| Glycerin | 75.8 |
| Water (distilled) | 10.1 |
| $ZnCl_2$ | 13.6 |
| Alcohol Extract of Periwinkle | 0.5 |

To prepare Additive A, the sodium bicarbonate is dissolved in the distilled water and this solution is added to the glycerin with stirring until a homogeneous solution is made. To this mixture is added the periwinkle extract and the mixture is stirred until all the periwinkle extract is incorporated.

To prepare Additive B, $ZnCl_2$ is dissolved in distilled water and the resulting solution is added to the glycerin with stirring and heated to 60° C. until a homogeneous solution is obtained. The periwinkle extract is stirred into the mixture until it is incorporated. The resulting Additive mixtures may then be used to formulate a toothpaste, mouthwash or other product. In the formulas given below, the percent by weight of periwinkle extract in the final product is listed. When preparing these formulations, however, it is more convenient, and therefore preferable, to add the ingredient in the form of one of the Additives.

EXAMPLE 1

Preparation of a toothpaste containing periwinkle extract and sodium bicarbonate.

| Materials | % by Wt. |
|---|---|
| Sodium Bicarbonate | 50 |
| Glycerin | 31.2 |
| Polyethylene Glycol Powder (CARBOWAX 3350 TM) | 5 |
| Polyethylene Glycol Liquid (CARBOWAX 400 TM) | 10 |
| Sodium Saccharin | 1.5 |
| Sodium Fluoride | 0.1 |
| Sodium Lauryl Sulfate | 0.8 |
| Flavoring | 1.0 |
| Periwinkle Extract | 0.4 |

The periwinkle Additive A as prepared above is added to glycerin, then the sodium bicarbonate is added and the mixture is stirred until a smooth paste is obtained. The CARBOWAX 3350 ® and CARBOWAX 400 ® are added and the mixture is stirred until all ingredients are completely incorporated. The flavoring, sweetener (sodium saccharin), sodium lauryl sulfate, and sodium fluoride are then added with stirring until a homogeneous mixture is obtained.

EXAMPLE 2

Preparation of a toothpaste containing periwinkle extract, sodium bicarbonate and aloe vera extract.

| Materials | % by Wt. |
|---|---|
| Sodium Bicarbonate | 35.0 |
| Glycerin | 22.8 |
| Water (distilled) | 10.0 |
| Calcium Carbonate | 10.0 |
| Aloe Vera Extract | 15.0 |
| Cellulose Gum | 2.0 |
| Sodium Lauryl Sulfate | 0.8 |
| Flavoring | 1.2 |
| Titanium Dioxide | 1.0 |
| Periwinkle Extract | 0.3 |
| Chlorophyllin Copper Complex | 0.7 |
| Tetrasodium Pyrophosphate | 1.2 |

To a mixture of glycerin and water are added sodium bicarbonate and calcium carbonate. This mixture is stirred until a smooth paste is obtained. Aloe vera extract and periwinkle Additive A are added with stirring until a homogeneous mixture is obtained. Cellulose gum, sodium lauryl sulfate, flavoring, titanium dioxide, chlorophyllin copper complex and tetrasodium pyrophosphate are then added and the mixture is stirred until the desired consistency is obtained.

EXAMPLE 3

Preparation of a toothpaste containing periwinkle extract and zinc chloride.

| Materials | % by Wt. |
|---|---|
| Glycerin | 19.0 |
| Polyoxyethylene 80 Sorbitan Monolauriate (POLYSORBATE 80 TM) | 2.0 |

| Materials | % by Wt. |
|---|---|
| Calcium Pyrophosphate | 5.0 |
| Sodium Lauryl Sulfate | 0.8 |
| Zinc Chloride | 0.1 |
| Flavoring | 0.6 |
| Dicalcium Phosphate | 27.0 |
| Calcium Carbonate | 24.2 |
| Periwinkle Extract | 0.3 |
| Water (distilled) | 21.0 |

To a mixture of glycerin and half the amount of deionized water are added the calcium pyrophosphate, dicalcium phosphate and calcium carbonate with stirring until a smooth paste is obtained. To this paste s added zinc chloride and periwinkle Additive B; these are incorporated into the paste until a homogeneous mixture is obtained. Finally the flavoring, sodium lauryl sulfate, POLYSORBATE 80® and the remaining water are incorporated with stirring to produce the desired consistency of toothpaste.

The above toothpastes when used in the normal manner one or more times per day are excellent cleansing agents and breath fresheners. When used over an extended period, the bleeding associated with vigorous brushing tends to be reduced, and the condition of the tissue appears to be benefited.

EXAMPLE 4

Preparation of an oral rinse containing periwinkle extract.

The extract of the periwinkle herb was combined with other ingredients usually found in oral rinse compositions to make product that exhibits properties superior to commercially available products.

| Marterials | % by Wt. |
|---|---|
| Ethyl Alcohol | 10.0 |
| Periwinkle Extract | 0.03 |
| Citric Acid | 0.03 |
| Flavoring oil of winter green | 0.25 |
| Glycerin | 3.79 |
| Water (distilled) | 85.00 |
| Sodium Lauryl Sulfate | 0.10 |
| POLYSORBATE 80 TM | 0.60 |
| Zinc Chloride | 0.20 |

In the formulation of the oral rinse and the toothpastes, it is preferable to include sudsing agents, such as sodium lauryl sulfate, to aid in the penetration of the film which forms on teeth. The sudsing agent carries the active ingredients into crevices in the mouth to sites where the active ingredients can attack plaque and bacteria. Suitable sudsing agents are those which are reasonably stable throughout a wide pH range. They may be nonsoap, nonionic, cationic or amphoteric organic synthetic detergents.

Test Results Demonstrating Plaque Reduction and Control of Volatile Sulfur Compounds The oral rinse prepared according to Example 4 with the Additive B containing an extract of periwinkle and $ZnCl_2$ and containing an appropriate sudsing agent exhibits properties beneficial to the teeth and other tissues of the oral cavity. For example, it is well known that without the removal or the deactivation of the sticky mass (plaque) that adheres to the teeth, the gums become sore and bleed easily when brushed. Therefore any agent that helps to reduce the level of this sticky mass is beneficial to the teeth and gums.

A comparison of test results of an oral rinse of this invention with a commercially available plaque reducing and malodor reduction rinse illustrates the effectiveness of the present invention against plaque and odor-forming bacteria.

Plaque Reduction

Plaque formation during a three day experimental period was compared in 2 males and 1 female volunteer using two compositions of the present invention and a placebo. The formula for the periwinkle and $ZnCl_2$ oral rinse is that given in Example 4. The other periwinkle rinse is of the same formulation, with periwinkle extract forming 0.03% by weight of the product, except that the $ZnCl_2$ is omitted. (The $ZnCl_2$ is also omitted from the Additive B preparation).

The teeth of all subjects were cleaned free of plaque and calculus corroborated by disclosure with the standard basic fuschin. This was followed by a three-day period of brushing with a commercial non-fluoride dentifrice and no use of the test mouthrinse. At the end o this period the plaque scores were determined using the method of Quigley and Hein. A score of 0 to 5 was assigned to each facial and lingual nonrestored surface using teeth 3, 9, 12, 25 and 29. In this manner a baseline was determined. After the baseline period each subject was assigned another blank control period and then two periods each on est and control mouthwashes.

During each 3 day trial period, with the exception of the two blank control periods, the subjects were instructed to use 20 ml of mouthwash as a rinse 2 times daily. At the end of the trial period plaque scores were again determined.

Results of this study are shown in Table 1.

TABLE 1

Plaque Indices and Percent Plaque Reduction of Periwinkle Oral Rinses
Scale = 0 to 5.0

| Group | Baseline (Day 0) | Post Treatment (Day 3) | Percent Reduction |
|---|---|---|---|
| Placebo | 2.58 | 2.88 | +11.63 |
| Periwinkle & $ZnCl_2$ | 2.64 | 2.15 | −18.56 |
| Periwinkle | 2.55 | 2.20 | −14.28 |

The effectiveness of the periwinkle oral rinse in controlling plaque growth was demonstrated as summarized in Table 1. The plaque score when the placebo was used did not drop but increased from 2.58 for a 11.63% plaque growth. The plaque scores with the zinc containing compound were reduced from 2.64 to 2.15, corresponding to a reduction of 18.56%. The difference between the two groups corresponds to a 30.19% difference between placebo and periwinkle rinse containing zinc. Users of the periwinkle rinse without $ZnCl_2$ also exhibited a significant lowering of the plaque scores, from 2.55 to 2.20, a 14.28% decrease which corresponds to a difference of 25.91% between the placebo and this rinse.

Control of Volatile Sulfur Compounds

It has been reported that volatile sulfur compounds (VSC) are produced in the oral cavity. I. has been stated that the tongue acts as a major reservoir of VSC and that these VSC originate mainly in salivary sediment, a mixture of cellular debris and microorganisms that use sediment constituents as proteinaceous substrates. The VSC so formed can be detected by using lead acetate-impregnated strips above the headspace of putrifying saliva, as well as by breath malodor. (Boulware and Southard, Compendium of Continuing Education in Dentistry, Supplement No. 5, 1984).

Aside from the obvious cosmetic implication of breath malodor, the presence of these reactive sulfides in the mouth can have significant physiologic consequences. For example, hydrogen sulfide, a well-known irritant which is produced in the oral cavity, has been implicated in the solubilization of gingival collagen and may even alter the permeability of the cervicular epithelium. Similarly, evidence suggests that methyl mercaptan inhibits the synthesis of protein and collagen at concentrations of 10 ng/ml. Control of these VSC found in the oral cavity would be desirable both for health and cosmetic reasons.

Two male subjects were asked to rinse with an oral rinse of the formula given in Example 4, "LISTERINE ®" mouthrinse (which is a mixture of essential oils) or water. Immediately before product use and before normal morning oral hygiene approximately 2 ml of saliva was collected in a 15×150 mm glass test tube and the tube was immersed in an ice bath. This procedure was repeated 45 minutes after product use. Crossover studies were conducted in which the procedure was repeated using "LISTERINE ®" as the test wash. The saliva samples were incubated at 25° C. for 24 hours with a lead acetate-impregnated test strip suspended in the head space. The lead acetate papers were read on an empirical scale of 0 to 3 as a function of discoloration. (This was the method of testing and scoring used by Boulware and Southard). The results are shown in Table 2.

TABLE 2

VSC Levels in Headspace Above Incubated Saliva
As Scored by Lead Acetate Papers:
Saliva Collected 45 Mins. After Oral Rinse
Scale = to 3.0

| Oral Rinse | VSC Score |
|---|---|
| Periwinkle & $ZnCl_2$ | 0.1 |
| "LISTERINE ®" | 2.4 |
| Water | 3.0 |

Clearly, the product containing the periwinkle extract was superior to the commercial available product. It was approximately 24 times more effective than "LISTERINE ®" when compared by this method.

Saliva Glycolysis Assay

The saliva glycolysis assay has been used to predict the clinical effectiveness of antiplaque agents. (Yankell, Compendium of Continuing Education in Dentistry, Supplement No. 5, 1984. Such studies are based on the fact that during glycolysis the bacteria of the oral cavity produce acidic by-products which lower the pH of 1hole saliva.

The study was performed to compare a placebo (water), "LISTERINE ®" and the oral rinse described in Example 4. Three subjects, 2 male and 1 female, were instructed to rinse with a test rinse. Four ml of saliva was collected from each person at 15 and 45 minutes after rinsing. Each saliva sample with the addition of 5% sucrose was incubated at 25° C. for 5 hours and the pH of the mixture recorded at 1 hour intervals. The study was done in a crossover design such that each person used each of the test solutions on different days.

The results of these experiments are shown in Tables 3 and 4.

TABLE 3 pH of Sample Collected 15 Minutes After Use of Rinse

| Times-Hrs. | 0 | 1 | 2 | 3 | 4 | 5 |
|---|---|---|---|---|---|---|
| Water | 6.3 | 5.6 | 5.3 | 5.0 | 4.9 | 4.7 |
| "LISTERINE ®" | 6.8 | 6.5 | 6.3 | 6.1 | 5.9 | 5.5 |
| Periwinkle & $ZnCl_2$ | 6.5 | 6.5 | 6.6 | 6.6 | 6.5 | 6.5 |

TABLE 4 pH of Sample Collected 45 minutes After Use of Rinse

| Times-Hrs. | 0 | 1 | 2 | 3 | 4 | 5 |
|---|---|---|---|---|---|---|
| Water | 6.2 | 6.2 | 5.7 | 5.4 | 5.0 | 4.9 |
| "LISTERINE ®" | 6.8 | 6.6 | 6.4 | 6.0 | 5.8 | 5.6 |
| Periwinkle & $ZnCl_2$ | 6.6 | 6.6 | 6.5 | 6.5 | 6.4 | 6.5 |

The periwinkle extract rinse was better able to retard the decrease in pH than were either "LISTERINE ®" or water. These results indicate that there is not only significant reduction in bacterial activity by using the periwinkle extract in an oral rinse but also that the beneficial effects of the extract continue in the saliva for some time after use. This ability of the periwinkle extract to be retained in the saliva is important because it provides protection for significant periods of time after use. The pH of samples collected 15 and 45 minutes after use of the periwinkle extract oral rinse was measured again 10 hours after use as 5.8 and 6.0, respectively. These results further demonstrate the long-lasting effect of the periwinkle extract oral rinse.

Antimicrobial Activity

The antimicrobial activity of periwinkle extracts against the following microorganisms was evaluated as described below.
1. Streptococcus salevarius ATCC 25975
2. Listeria monocytogenes ATCC 7644
3. Bacteroides melaninogenicus ATCC 25845
4. Bacteroides vulgatus ATCC 8482
5. Escherichia coli ATCC 8739
6. Streptococcus faecalis ATCC 8043

Extracts were prepared, as previously described using each of the following extractants:
1. Ethanol
2. Methanol
3. Propanol
4. Isopropanol
5. Water In order to quantitatively assay each of the above extracts and comparatively evaluate their antimicrobial properties, the above extracts, submitted in dry form, were reconstituted. To obtain concentrations of 100 mg. per ml., in their respective extract solvents, 100 ul. of each of the test materials was spotted on a 10 mm. paper disk and airdried.

Disks impregnated with the extracts 1ere than placed on nutrient agar (Difco) and/or blood agar plates (BBL) and seeded with $n \times 10^4 - 10^5$ cells per ml. of the above organisms. After overnight incubation at 35° C. the assay plates were evaluated for zones of inhibition.

Of the five extracts tested on disks some activity was noted for the ethanol and methanol extracts against B. vulgatus, S. faecalis and S. aureus. Other organisms such as *E. coli* and *B. melaninogenicus* were not affected. In every instance the ethanol extract appeared to be more potent. The propanol and isopropanol extracts exhibited no antimicrobial activity against the named organisms.

In order to utilize a larger, more concentrated quantity of the ethanol extract, a solution containing 200 mg./ml. of the crude ethanol extract was prepared in 0.05 M. $KH_2PO_4$ buffer, pH=4.5. Holes, 10 mm. in diameter, Were punched into nutrient agar and/or 5% defibrinated sheep blood agar plates and filled with approximately 0.2 ml. of test material.

The results show that the crude ethanol extract was active against *L. monocytogenes* and *B. vulgatus*. ,he ethyl alcohol extract also was active against *S. salevarius*.

In another series of tests, the ethanol extract of periwinkle was submitted to a microbiological laboratory for assessment of its activity against specific microorganisms associated with dental plaque and oral disease. A standard plate technique was used, in which the zone of inhibition of microbial growth around a well containing the extract was measured. Antimicrobial activity was demonstrated against the following: *Bacteroides melanogenicus*, an anaerobic gram-negative species; *Streotococcus mitis* and *S. salivarius*, gram-positive microorganisms related to *S. mutans*, a major resident of dental plaque and associated definitively with the incidence of dental caries. The ethanol extract was not active, under the conditions used, against yeast (*Candida albicans*) or *Lactobacillus acidophilus*.

Anionic Wetting Agent

The effectiveness of the ethanol extract of periwinkle against Listeria Monocytogenes appears to be greatly enhanced when an anionic surfactant such as sodium lauryl sulfate is present in the rinse or toothpaste formulated with the extract as may be seen from the following data.

Using Listeria Monocytogenes

Serial dilutions were prepared using the ethanol periwinkle extract alone, Sodium Lauryl Sulfate (Sigma #L4509) at 0.25%, 0.10% and 0.05% final concentrations and methanol extract plus the above three concentrations of sodium lauryl sulfate. All dilutions were prepared in Tryppticase soy broth (Difco).

A mid-log phase culture of Listeria monocytogenes ATCC 7644 was prepared. Cells were washed and adjusted to achieve an inoculum of $N \times 10^6$ cells/ml.

Ten microliters of the resulting organism suspension was used to inoculate 400 ul of each test medium to achieve a final concentration of $N \times 10^4$ cells per cavity.

The test system was incubated at 35° C. for 18 hours. Wells which showed complete clearing at the highest dilution were taken as the minimum inhibition concentration.

The results are shown in the following table.

| | \multicolumn{13}{c}{Well Number Dilution} | |
|---|---|---|---|---|---|---|---|---|---|---|---|---|---|
| | 1 1/1 | 2 1/2 | 3 1/4 | 4 1/8 | 5 1/16 | 6 1/32 | 7 1/64 | 8 1/128 | 9 1/256 | 10 1/512 | 11 1/1024 | 12 1/2048 | Control +++ |
| Ethanol Extract | * | * | [*] | * | — | — | — | — | — | — | — | — | |
| SLS 0.25 | * | * | * | [*] | * | — | — | — | — | — | — | — | |
| SLS 0.10 | * | [*] | * | — | — | — | — | — | — | — | — | — | |
| SLS 0.05 | [*] | * | — | — | — | — | — | — | — | — | — | — | |
| SLS 0.25 Extract | * | * | * | * | [*] | * | — | — | — | — | — | — | |
| SLS 0.10 Extract | * | * | * | [*] | * | — | — | — | — | — | — | — | |
| SLS 0.05 Extract | * | * | [*] | * | — | — | — | — | — | — | — | — | |

Activity profile against *Listeria monocytogenes* ATCC 7644

\* complete clearing

☐ minimum bacteriocidal concentration (—) growth

Anionic surfactants which can be used in the invention include the water-soluble salts of alkyl sulfates with from 10 to 18 carbon atoms in the alkyl radical. A preferred group of anionic surfactants is mixtures ,f fatty and alcohol sulfates containing more than 50% $C_{12}$ and $C_{14}$ chains. The preferred surfactant is sodium lauryl sulfate. Anionic surfactants such as sodium dodecyl benzenesulfonate, sodium lauryl sarcosinate and sodium monoglyceride sulfonate may also be used, so long as they are physiologically acceptable when used in the oral cavity.

The anionic surfactant is added at a level of about 0.03% to 3%. The amount employed is determined by the level which is needed to synergistically increase the activity of the periwinkle extract. It is also determined by the potential of the surfactant to irritate oral tissues. In general, a maximum of 3% surfactant can be employed depending on the specific irritation potential of the surfactant.

Another consideration is the ability of anionic surfactants to produce foam. Foaming is a highly desirable attribute of oral products such as toothpaste and mouthwash. However, excessive foaming can be a negative to the average consumer. The amount of surfactant used is that amount necessary for increased activity of the periwinkle extract, but not so much as to create an undesirable level of foaming during use of the product or irritation of oral tissues.

OPTIONAL INGREDIENTS

The combination of periwinkle extract and anionic surfactant can be formulated into compositions including mouthwashes, liquid dentifrices and toothpaste. Particular formulations are shown in the examples below. The mouthwashes contain flavoring oils and appropriate nonionic surfactants to maintain them in dispersion if the anionic surfactant itself is unable to do so. Color may be added, if desired. The toothpastes additionally contain abrasive materials (to remove stained pellicle), as well as flavor oils, humectants, and binders. The compositions may also contain water, fluoride and additional antiplaque and antimicrobial agents.

Mouthwash formulations will preferably contain water, humectants, thickening agents, flavor and color. The humectants useful in the present invention include glycerin, sorbitol, and propylene glycol. These materials act to give body to the composition, and to prevent crystallization of solid material around the opening of the container which could interfere with easy removal of the cap of the container.

Flavoring agents can also be added to the compositions of the invention. Acceptable agents include sweeteners, oil of peppermint, oil of spearmint, oil of wintergreen, oil of cinnamon and oil of clove. Suitable nonionic dispersants for the flavor oils in mouthwashes include the polyethylene oxide condensates of alkyl phenols, block copolymers resulting from the condensation of ethylene oxide with the reaction product of propylene oxide condensation, and polyoxyethylene derivatives of sorbitan fatty acid condensates, also known under the trade name "PLURONICS". Sweeteners that may be incorporated include saccharin, dextrose, sodium cyclamate, and acesulfam. The amounts of flavor oil used generally are incorporated at levels of about 0.03% to about 2%. Sweetening agents are generally added to a level of about 0.1% to 5%.

In liquid dentifrices or toothpastes it is useful to incorporate a dental abrasive. Silica dental abrasives are among the preferred abrasives for this invention. The silica abrasive polishing agent generally has an average particle size ranging from about 0.5 to 35 microns, preferably between about 5 and 15 microns The dental abrasive preferably is amorphous, and can be precipitated silicas or silica xerogels as described in Pader et al., U.S. Pat. No. 3,538,230, issued Mar. 2, 1970. The preferred silicas are silica xerogels marketed under the trademarks "SYLODENT®" and "SYLOID®" by W. R. Grace and Company, Davison Chemical Division. Precipitated silicas such as those marketed under the trademark "ZEODENT®" by the J. M. Huber Corporation are also useful in the dentifrices of the present invention.

Other dental abrasives are useful in the current invention. Among these are suitable particulate resins, including, for example, malamines, phenolics, melamine-ureas, melamine formaldehydes, urea-formaldehydes, cross-linked epoxies, and cross-linked polyesters. Also suitable are alumina trihydrates, calcium phosphates, including dicalcium phosphate dihydrate, anhydrous dicalcium phosphate and betaphase calcium pyrophosphate. Also useful are calcium carbonate abrasives and the insoluble metaphosphates, such as insoluble sodium metaphosphate. The amount of abrasive can range up to about 75% by weight of the dentifrice. Preferably, toothpastes contain about 5% to 50% by weight of the abrasive.

The abrasives noted can be supplemented or replaced by more soluble abrasive products such as sodium bicarbonate having an average particle size from about 1 to 50 microns. Sodium bicarbonate is preferred as a sole or adjunct abrasive in some formulations comprising periwinkle extract. Sodium bicarbonate is useful for toothpaste and liquid dentifrice preparations used in certain treatment and maintenance regimens for patients with periodontal diseases. While sodium bicarbonate can be employed as the sole abrasive, it is preferably supplemented with a silica xerogel or silica precipitate in the present invention.

Binding agents are also useful for the toothpastes of the current invention. Among the binders that can be used are, for example, carrageenan (Irish moss, carboxymethyl cellulose, xanthan gum, carboxyvinyl polymers, locust bean gum, and cellulose ether polymers. The binders are generally incorporated at a level of about 0.1 to 2%.

A further optional ingredient for the compositions of the invention is a fluoride source. Preferred sources of fluoride are sodium monofluorophosphate and sodium fluoride. Also useful are stannous fluoride and other fluoride salts such as ammonium fluoride, stannous fluorozirconate, titanium fluoride and others. The total number of useful fluoride compounds is large, and includes those disclosed in U.S. Pat. No. 4,515,772, May 7, 1985incorporated herein by reference. Sodium fluoride and sodium monofluorophosphate are the preferred fluoride sources.

Other optional antiplaque and antimicrobial agents may be incorporated into the compositions of this invention. Among these are soluble zinc salts such a zinc chloride and insoluble zinc salts such as zinc citrate Also useful are antimicrobial phenolic compounds such as thymol. These latter compounds have but limited antimicrobial activity in the oral cavity when present in concentration which are organoleptically pleasant. If present, these compounds generally comprise up to about 5% of the weight of the dentifrice.

Optional antimicrobial agents also include cationic bisbiguanide materials such as chlorhexidine, octenidine, and the like. These compounds, however, must be selected with the understanding that they are compatible with, i.e. are not inactivated by, the anionic surfactant which is an essential component of the present invent on. The cationic surfactants and antimicrobial agents commonly available will introduce an unpleasant, bitter flavor into the products of the current invention if they are not inactivated by the anionic surfactant essential to enhancement of the activity of the periwinkle extract. Their utility in the current invention is therefore limited to those compositions wherein a cationic and an anionic surfactant are compatible. That such compatibility occurs is demonstrated in numerous marketed conditioning shampoo composition, as well as the reported compatibility of sodium lauryoyl sarcosinate and octenidine. Tests for compatibility are conducted simply by techniques well known to those skilled in assessment of antimicrobial potency.

The compositions usually have a pH of about 5 to about 10, preferably between pH 6 and pH 9.

The compositions of the current invention are applied to the oral cavity in the conventional manner. They are manufactured by techniques commonly used by the oral care formulation art.

The present invention can be used in several forms, and has numerous beneficial effects on oral hygiene. The invention should not be considered to be limited to the specific formulas given herein, but rather as encompassing equivalent preparations.

Having now described preferred embodiments of the invention it is not intended that it be limited except as may be required by the appended claims.

I claim:

1. An oral hygiene method for reducing plaque and for the treatment of periodontal diseases of bacterial etiology, the method comprising reducing bacterial activity in the oral cavity by applying to the oral cavity a composition containing from about 0.03% to about 50% by weight of the total composition, a dried ethanol extract from the perennial herb periwinkle.

2. An oral hygiene method for reducing plaque and for the treatment of periodontal diseases of bacterial etiology, the method comprising reducing bacterial activity in the oral cavity by applying to the oral cavity a composition containing from about 0.03% to about 10% by weight of the total composition, a dried ethanol extract from the perennial herb periwinkle.

3. The method of claim 2 wherein the extract is taken up in a carrier.

4. The method of claim 3 wherein the carrier is a liquid selected from the group consisting of water, glycerin and lower alcohols.

5. The method of claim 1 wherein the composition is in the form of an oral rinse composition.

6. The method of claim 1 wherein the composition is in the form of a toothpaste composition.

7. The method of claim 1 wherein the composition includes an anionic surface active agent.

8. The method of claim 7 wherein the surface active agent is sodium lauryl sulfate.

* * * * *